(12) United States Patent
Purola

(10) Patent No.: US 8,952,202 B2
(45) Date of Patent: *Feb. 10, 2015

(54) MULTISTAGE CUMENE OXIDATION

(75) Inventor: Veli-Matti Purola, Hamari (FI)

(73) Assignee: Borealis AG, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 13/139,932

(22) PCT Filed: Dec. 17, 2009

(86) PCT No.: PCT/EP2009/009121
§ 371 (c)(1),
(2), (4) Date: Jul. 12, 2011

(87) PCT Pub. No.: WO2010/078934
PCT Pub. Date: Jul. 15, 2010

(65) Prior Publication Data
US 2011/0263905 A1 Oct. 27, 2011

(30) Foreign Application Priority Data
Dec. 17, 2008 (EP) .................................. 08171941

(51) Int. Cl.
*C07C 409/10* (2006.01)
*C07C 407/00* (2006.01)

(52) U.S. Cl.
CPC ............. *C07C 409/10* (2013.01); *C07C 407/00* (2013.01)
USPC ............ 568/569; 568/385; 568/558; 568/571

(58) Field of Classification Search
USPC .................................. 568/569, 558, 385, 571
See application file for complete search history.

(56) References Cited

U.S. PATENT DOCUMENTS

| 5,908,962 | A | 6/1999 | Zakoshansky et al. | |
|---|---|---|---|---|
| 6,225,513 | B1 | 5/2001 | Zakoshansky et al. | |
| 6,465,695 | B1 | 10/2002 | Fulmer | |
| 7,312,365 | B2 | 12/2007 | Black | |
| 7,393,984 | B1 * | 7/2008 | Zakoshansky et al. | ....... 568/569 |
| 2009/0171126 | A1 | 7/2009 | Zakoshansky et al. | |

FOREIGN PATENT DOCUMENTS

| EP | 0816335 | A1 | 1/1998 | |
|---|---|---|---|---|
| GB | 1006319 | A | 9/1965 | |
| JP | 4305564 | A | 10/1992 | |
| JP | 2000-290249 | | * 10/2000 | ............ C07C 407/00 |
| JP | 2000-302752 | | * 10/2000 | ............ C07C 407/00 |
| JP | 2000290249 | A | 10/2000 | |
| JP | 2000302752 | A | 10/2000 | |
| JP | 2003231674 | A | 8/2003 | |
| WO | WO2009080341 | A1 | 7/2009 | |

OTHER PUBLICATIONS

International Search Report and Written Opinion for Application No. PCT/EP2009/009121 dated Jun. 4, 2010.
Office Action for U.S. Appl. No. 13/140,042 dated Feb. 11, 2013.
Office Action for U.S. Appl. No. 13/140,042 dated Oct. 16, 2013.
Sunoco/UOP Phenol Process, UOP LLC, 2004.
Weber, Large Bubble Columns for the Oxidation of Cumene in Phenol Processes, Chem. Eng. Technol. 25(5):553-558, 2002.
Weber et al., Phenol, Wiley-VCH Verlag GmbH & Co. KGaA, Weinheim, pp. 1-17, 2005.

* cited by examiner

*Primary Examiner* — Sudhakar Katakam
*Assistant Examiner* — Pancham Bakshi
(74) *Attorney, Agent, or Firm* — Meunier Carlin & Curfman, LLC

(57) ABSTRACT

The present invention concerns a process for oxidizing cumene to cumene hydroperoxide using an oxygen containing gas, preferably air, which process comprises —conducting a cumene feed and an oxygen containing gas feed to at least the first oxidation reactor in a series of 3-8 reactors, thereby forming an oxidation mixture, and conducting the formed oxidation mixture from one reactor to the next, preferably after an oxidation reaction has taken place, wherein —the reactors comprise at least one lower pressure oxidizer (1) as the first reactor in the series and at least one higher pressure oxidizer (2) as the last reactor in the series; —any lower pressure oxidizer is operated at a pressure of at least atmospheric pressure and any higher pressure oxidizer is operated at a pressure of at least 0.5 bar higher than said at least one lower pressure oxidizer.

13 Claims, 1 Drawing Sheet

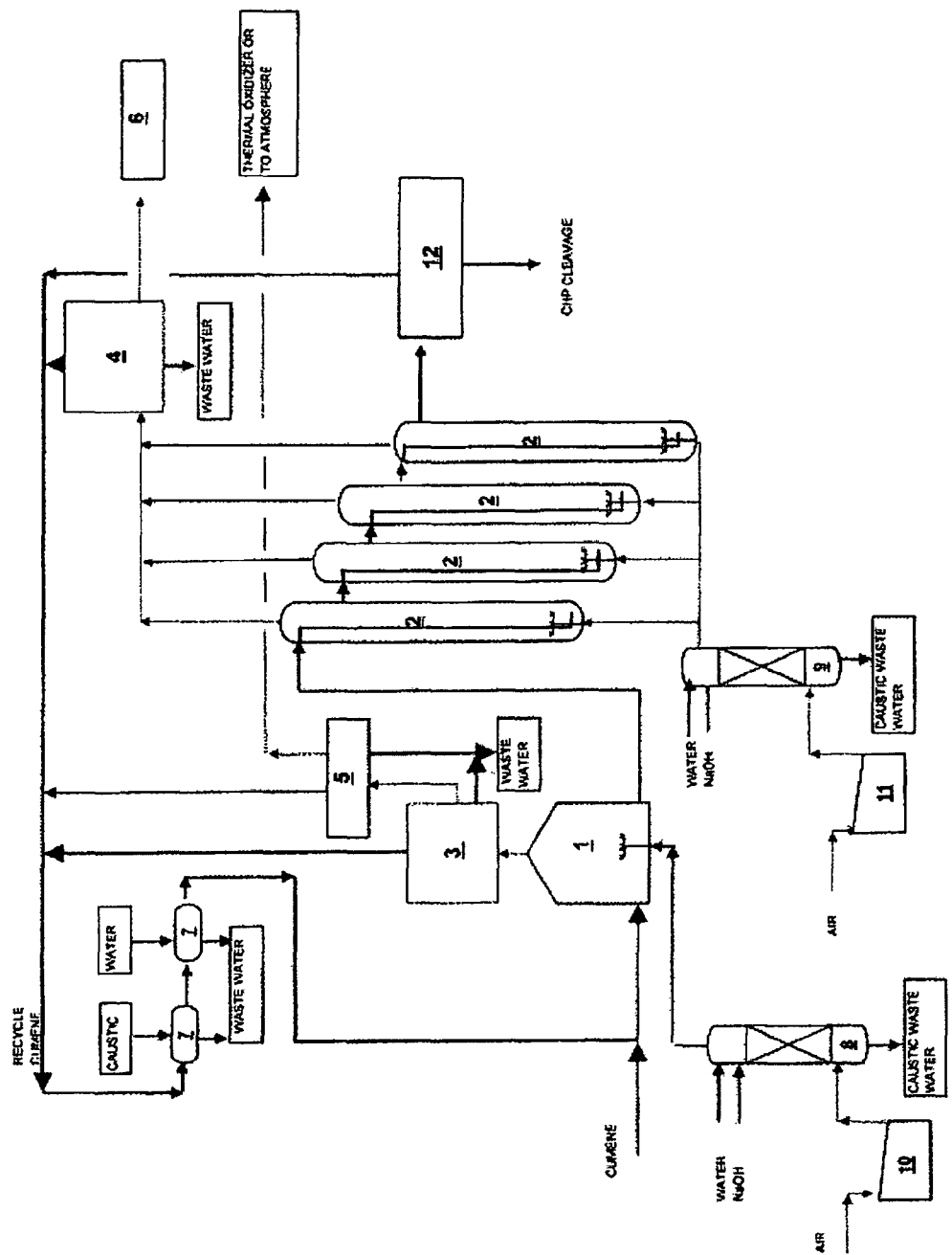

MULTISTAGE CUMENE OXIDATION

CROSS REFERENCE TO RELATED APPLICATIONS

This application is a 35 USC 371 national phase of International Application No. PCT/EP2009/009121 filed Dec. 17, 2009, which claims priority to European Patent Application No. 08171941.1 filed Dec. 17, 2008, the contents of all of which are hereby incorporated herein by reference in their entirety.

BACKGROUND OF THE INVENTION

1. Field of the Invention

The present invention concerns a process for the oxidation of cumene to cumene hydroperoxide, in which the configuration of the process has been improved.

2. Description of Related Art

Phenol is commonly manufactured through a cumene procedure, wherein cumene is oxidized to cumene hydroperoxide (CHP) and the resulting oxidation product mixture is concentrated and subjected to a cleavage reaction. Subsequently, the cleavage product mixture is conducted to a distillation section, wherein the main products of the cleavage reaction, i.e. phenol and acetone, are first separated and then purified through a series of distillation steps or other purification steps.

In the prior art, oxidation of cumene is generally carried out using a so-called wet-oxidation procedure, in which oxidation takes place in solution with the help of an aqueous solution of, for example, a carbonate. Dry oxidation procedures, where the only compounds introduced into the reaction mixture are the starting material (cumene) and the oxidation gas, are becoming more common. A disadvantage of the wet procedures is that they require, among others, a step of removing the carbonate and neutralizing the aqueous oxidized mixture, which has been rendered alkaline by the carbonate, before the oxidation product (CHP) can be concentrated.

The liquid phase oxidation of cumene is explained in terms of a radical mechanism by Kazua Hattori et al. in Journal of Chemical Engineering of Japan, vol. 3, no. 1, (1970), p. 72-78. The main side products formed in the oxidation are acetophenone and carbinol.

The process is generally thought to follow the following scheme

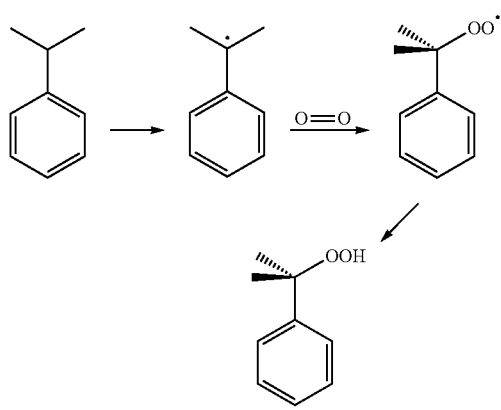

The formation of acetophenone (AcPh) is problematic, since it is not separated from the product mixture downstream from the oxidation. Carbinol, particularly dimethyl benzyl alcohol (DMBA), is partly recovered by converting it to α-methyl styrene (AMS) and by the subsequent hydrogenation of AMS to cumene. However, AMS as such is a source of heavy products, such as AMS dimers, which are not recovered downstream.

Selectivity is normally calculated on a molar basis from the cumene oxidation products:

2CHP/(CHP+AcPh+DMBA+2DCP)

(DCP=dicumyl peroxide.) Typical values for the total selectivity in the oxidation are in the range of 92-94%.

Operation and design parameters of the oxidation, such as the pressure, the temperature, the CHP concentration, the residence time, the number of reactors, the treatments of the recycle streams, the treatments of the off-gas and the cooling of the reactors, have an effect on the selectivity. Thus, the right combination of these parameters is important. It is also important that the feeds of cumene and air are properly treated to remove inhibitors, such as phenol, AMS, sulphur and carbon dioxide, or other impurities, such as inorganic acids or bases or free-radical generating compounds, since these impurities may cause the premature decomposition of the newly formed CHP. Premature decomposition of the CHP may also be caused by excess use of pumps.

Oxidation of cumene into cumene hydroperoxide (CHP) has been thoroughly described in the prior art (as in GB 1006319, JP 4305564, JP 2000290249, JP 2000302752 and JP 2003231674), but there is still a need for further improving the process by improving the combination of parameters.

Improvements have been attempted in the prior art, for example, by positioning the oxidation reactors at reducing elevations, as in JP 2000290249, whereby the need for pumps or other similar means for moving the oxidation reaction mixture from one reactor to the next is removed, or by making the capacity of the oxidation reactors smaller one by one, as in JP 2000302752, whereby the reaction rate will be highest in the first reactor. In JP 2003231674, it has been attempted to optimize the oxidation reaction by limiting the velocity of the oxygen-containing gas bubbled through an oxidation reactor.

SUMMARY OF THE INVENTION

It is an aim of the present invention to provide an improved process for the oxidation of cumene.

Particularly, it is an aim of the present invention to provide an oxidation process, wherein advantageous process parameters are combined in a new and inventive way.

These and other objects, together with the advantages thereof over known processes, are achieved by the present invention, as hereinafter described and claimed.

The present invention concerns a process for oxidizing cumene into cumene hydroperoxide using air or other oxygen containing gas. The present invention also concerns an apparatus suitable for said oxidation.

More specifically, the process, apparatus and use of the present invention are defined in the claims. Thus, viewed from one aspect the invention provides a process for oxidizing cumene to cumene hydroperoxide using an oxygen containing gas, preferably air, which process comprises conducting a cumene feed and an oxygen containing gas feed to at least the first oxidation reactor in a series of 3-8 reactors, thereby forming an oxidation mixture, and
conducting the formed oxidation mixture from said reactor to at least one subsequent reactor wherein the reactors comprise at least one lower pressure oxidizer (1) as the first reactor in the series and at least one higher pressure oxidizer (2) as the last reactor in the series;

said at least one lower pressure oxidizer is operated at a pressure of at least atmospheric pressure and said at least one higher pressure oxidizer is operated at a pressure of at least 0.5 bar higher than said at least one lower pressure oxidizer.

Viewed from another aspect the invention provides a process for oxidizing cumene to cumene hydroperoxide using air, which process comprises conducting a cumene feed and an air feed to the bottom section of each oxidation reactor in a series of 3-8 reactors, thereby forming an oxidation mixture, and conducting the formed oxidation mixture from one reactor to the next after an oxidation reaction has taken place, characterized by the reactors consisting of low-pressure oxidizers (1) in the beginning of the series and high-pressure oxidizers (2) in the end of the series, the low-pressure oxidizers being operated at a pressure of at least atmospheric pressure and the high-pressure oxidizers being operated at a pressure of at least 1 bar higher than said low-pressure oxidizers.

It will be appreciated that the terms reactor and oxidizer are used interchangeably herein. Considerable advantages are obtained by means of the invention. Thus, the present invention provides an oxidation process, wherein the process stages with low CHP concentrations can be operated with high temperatures, large vessels, long residence times, small structural pressures and a low-pressure air compressor, thus focusing mainly on maximizing the CHP concentration and minimizing the formation of light and acidic impurities, such as formic acid, whereas the process stages with higher CHP concentrations can be operated with higher temperatures, smaller vessels (and smaller liquid inventories), shorter residence times, avoiding the use of pumps in liquid transfer and avoiding the use of adsorbers, such as carbon beds, in treating the off-gases, thus focusing mainly on a high selectivity without loss of valuable compounds and an improved safety.

Next, the invention will be described more closely with reference to the attached drawings and the following detailed description.

BRIEF DESCRIPTION OF THE DRAWINGS

FIG. 1 depicts the process and the apparatus according to a preferred embodiment of the present invention, for oxidizing cumene to cumene hydroperoxide using air.

DETAILED DESCRIPTION OF THE PREFERRED EMBODIMENTS OF THE INVENTION

The present invention concerns a process for oxidizing cumene to cumene hydroperoxide using an oxygen containing gas such as air. The oxygen containing gas feed is preferably air. However, a more concentrated oxygen gas may be used. The oxygen content of the oxygen containing gas may be up to 100%, preferably about 22-80% oxygen. The other components of the oxygen containing gas feed should be inert gases, typically nitrogen. In a preferred embodiment, air is used without modification (i.e. without an oxygen enrichment) other than the cleaning/purification procedures documented below.

The process of the invention comprises conducting cumene to at least the first reactor in the series. Typically this cumene feed is quite pure and essentially contains cumene and minor amounts of impurities. Preferably therefore, this feed is at least 95 wt % cumene, preferably at least 99 wt % cumene. It may contain recycled cumene as explained in further detail below or recycled cumene may be fed separately to the first (or other) reactors in the series. This cumene feed is preferably a liquid feed. Whilst this fresh cumene feed can be fed to more than one reactor in the series, it is especially preferred if fresh cumene (i.e. cumene not part of the oxidation mixture) is fed to the first reactor only.

Along with cumene, an oxygen containing gas is also feed to at least the first reactor in the series to thereby form an oxidation mixture. The cumene feed and oxygen containing gas feed are preferably fed separately although conceivably these could be fed together.

Once the oxidation mixture is formed in the first reactor, CHP forms. That part of the oxidation mixture which is displaced by the liquid being fed into a reactor is then conducted from the first reactor to at least one subsequent reactor, preferably the next one in the series. It is within the scope of the invention however for the oxidation mixture to be split and fed to one or more subsequent reactors. It is also within the scope of the invention for some transfers to occur in series and some transfers to be split and fed to different reactors.

Thus reactors can be arranged in parallel or in series or a mixture thereof. Other than in the last reactor, oxidation mixture from a reactor should be transferred to at least one downstream reactor in the series. Oxidation mixture from each reactor is preferably transferred to at least the next reactor downstream thereof in the series.

The reactors in the process of the invention are preferably connected only in series so that the oxidation mixture passes from one reactor to the next one in the series. It will be appreciated that the process of the invention will run continuously so there will always be new feed material entering and reacted material leaving the reactor.

Thus, to each subsequent reactor in the series (i.e. not the first), material is preferably transferred from the previous reactor. Thus, a liquid feed comprising unreacted cumene, its oxidation product and impurities is preferably fed from reactor to reactor in the series as the oxidation mixture. Thus, whilst cumene is formally transferred to each reactor in the series, it is preferably only the first reactor that has a dedicated and preferably essentially pure cumene feed. To all other reactors, any cumene is preferably added only as an unreacted part of the transferring oxidation mixture and that is not considered a "cumene feed" herein.

It will be appreciated that the amount of cumene in the oxidation mixture will reduce as the oxidation mixture passes from reactor to reactor as more cumene is converted to CHP and more removed from the top gases. As the reaction progresses therefore, each transfer mixture preferably contains less cumene and more CHP than the previous transfer mixture.

An oxygen containing gas is also fed, preferably to the bottom section, of each oxidation reactor, in the series of 3-8 reactors, thereby maintaining an oxidation mixture in each reactor. Unlike cumene therefore, fresh oxygen containing gas is preferably added to every reactor in the series. The oxidation mixture feed and oxygen containing gas feed are preferably fed separately although conceivably these could be fed together.

Typically residence time in the lower pressure reactors are 1 to 4 hours. Typically residence time in the higher pressure reactors are 1 to 4 hours.

It is preferred if the cumene feed enters the bottom section of the first lower pressure reactor although this is by no means critical. The term "bottom section" of a reactor will be readily understood by the skilled man. This means less than halfway up (vertically) the reactor in question.

It is also preferred if the oxygen containing gas feed enters the bottom section of the first lower pressure reactor. It is preferred if an oxygen containing gas is fed to all reactors in the series, ideally to the bottom section of all those reactors. Ideally, all reactors in the series are therefore fed with fresh oxygen containing gas.

Material transferred from any reactor to the next reactor in the series may be fed to any point of the next reactor but preferably the oxidation mixture is fed to the bottom section of the next reactor. This transfer may occur within the reactor itself as the conduit between reactors may pass through the top section of the next reactor and down the length of the next reactor (inside the next reactor) towards the base thereof. This is illustrated in FIG. 1.

At least the first reactor at the beginning of the series is a lower pressure oxidizer, while at least one subsequent reactor is a higher pressure oxidizer. Any lower pressure oxidizer is operated at a pressure of at least atmospheric pressure. Any higher pressure oxidizer is operated at a pressure of at least 0.5 barg higher, preferably more than 1 barg higher, than said lower pressure oxidizer. Where there are multiple lower and higher pressure reactors, it will be appreciated that the pressure in any higher pressure reactor must be at least 0.5 barg higher than the highest pressure in any of the lower pressure reactors.

By "lower pressure" is preferably meant a pressure of atmospheric pressure up to 3.0 barg preferably 0.01-3.0 barg, more preferably 0.01-2.0 barg, such as 0.05 to 1.5 barg. Preferably, any lower pressure oxidiser is operated at around atmospheric pressure, e.g. the atmospheric pressure prevailing where the reactor is located.

By "higher pressure" is preferably meant 1.01-10.0 barg, preferably 2.0-8.0 barg, more preferably 2.5-6.0 barg, and most preferably 3.0-4.5 barg.

It is appreciated that there is overlap between the ranges here. It will be appreciated therefore that for any higher pressure oxidizer to have a pressure of 1.5 barg it will be required that the pressure in the lower pressure oxidizer (s) is 1.0 barg or less and so on.

In a further highly preferred embodiment, any lower pressure reactor operates at a pressure of 0.01 to 2.0 barg and any higher pressure reactor operates at a pressure of 3.0 to 4.5 barg.

The number of lower and higher pressure reactors can vary. There must however be at least one of each. Ideally, there are one or two lower pressure reactors at the start of the series (reactors 1 and 2). Most preferably, the first reactor is a lower pressure reactor and is the only lower pressure reactor employed.

The number of high pressure reactors is preferably 2 or more, such 3 to 5, preferably 4. The preferred number of total reactors is preferably 5 or 6. The most preferred set up involves one lower pressure oxidizer followed by four higher pressure oxidizers.

It will be appreciated that where there are multiple lower pressure reactors, there is no requirement for them all to be operated at the same pressure. Similarly, where there are multiple higher pressure reactors there is no requirement for them all to be operated at the same pressure.

It is preferred, however, is that the lowest pressure in any higher pressure reactor is at least 0.5 bar higher than the highest pressure in any lower pressure reactor.

Where there are multiple lower pressure oxidizers it is preferred if these are all operated at the same pressure, more preferable around atmospheric pressure.

Higher pressure oxidizers can be operated at different pressures. It is preferred however, if the pressure in the higher pressure reactors is the same in all reactors.

According to a preferred embodiment of the present invention, where there are several high pressure oxidizers, in particular those with the same pressure, these operate with reducing liquid levels. In the context of the present invention, the term "reducing liquid levels" means that the upper surface of the oxidation mixture gets lower in each oxidation reactor following the first high pressure one. The term is not intended to limit the way in which the reactors are positioned, although the reactors may be placed at reducing heights relative to sea level. The term reducing liquid levels does not therefore mean less oxidation mixture is present, only that the upper surface of the oxidation mixture is lower relative to sea level than the previous oxidizer.

According to a preferred embodiment of the invention, in particular when the pressures between high pressure reactors are the same, the oxidation mixture passes from onwards by gravity, whereas from a lower pressure reactor, the oxidation mixture may be passed from one reactor to the next one using a pump. Preferably, the mixture passes from the last lower pressure reactor to the first higher pressure reactor using a pump.

According to another preferred embodiment of the invention, the off-gases are separated from the oxidation mixture at the top section of each reactor, after which they are combined and cooled, whereby a condensate containing unreacted cumene is formed. This cumene condensate may be washed and recycled to the cumene feed.

In the present invention, impurities, such as formic acid, methanol, formaldehyde or other components, whose vapour liquid equilibrium (VLE) favours their separation from the cumene and the CHP at a low pressure, and which may enter the reactors with the feed or may be formed in the reactors during the oxidation, are stripped from the oxidation mixture together with the oxidation gas in any lower pressure oxidizers.

Acidic components are partly condensed and neutralized in the off-gas condensing system. A caustic wash performed on the cumene, which has been separated from the off-gases by condensing, removes the acids as well as other water-soluble components, which may have an effect on the oxidation.

The apparatus of the present invention preferably contains the following parts (FIG. 1):

1 Lower pressure oxidizer
2 Higher pressure oxidizers
3 condenser(s) for lower pressure oxidation off-gases
4 condenser(s) for higher pressure oxidation off-gases
5 carbon adsorber
6 thermal oxidizer Further, the apparatus may be combined with the following (FIG. 1):

7 cumene wash
8 two-stage air scrubber for lower pressure air
9 two-stage air scrubber for higher pressure air
10 lower pressure air compressor
11 higher pressure air compressor
12 CHP concentration section The apparatus thus contains a series of 3-8 oxidizing reactors, of which one or more, preferably one to three, are lower pressure oxidizers 1, preferably in the form of tanks or vessels, and the remaining ones are higher pressure oxidizers 2, preferably in the form of columns. Each reactor 1, 2 can be provided with an air sparger in the bottom of the reactor 1, 2 for evenly distributing the air conducted into the reactor 1, 2. The oxidation mixture can be passed to each reactor 1, 2 through any part of the reactor, e.g. the bottom or top of the subsequent reactor 1, 2. Preferably, the oxidation mixture is transferred from the top of any oxidizer to the bottom of the next oxidizer.

Since oxidation is an exothermic reaction, the reactors 1, 2 may require external cooling. Therefore, each reactor 1, 2 may be equipped with a cooling system for the oxidation mixture. Preferably, internal cooling coils are used in the higher pressure reactors 2 to avoid further pumping of the oxidation mixture.

According to a preferred embodiment, the higher pressure oxidizers 2 are operated with reducing liquid levels so that the first higher pressure oxidizer is operated with the highest liquid level.

According to another preferred embodiment of the present invention, the apparatus further comprises at least one, preferably at least two, off-gas condensers 3, 4 equipped with a caustic injection and a condensate wash, for condensing the cumene and the other organic components that follow the air to the top section of the reactors 1, 2. One off-gas condenser 3 or 4 may be connected to each reactor 1, 2, or there may be one condenser 3 for the combined off-gases of the lower pressure oxidizers 1 and one condenser 4 for the combined off-gases of the higher pressure oxidizers 2.

The condensate from the off-gas condensers 3, 4 is preferably washed with a caustic solution in the condenser 3, 4 before being conducted further to the cumene wash 7, for washing recycled cumene.

According to another embodiment of the invention, the off-gases conducted from the oxidation, and optionally from the off-gas condensers 3, 4, may be further conducted to a cumene recovery system. An example of such a system is a carbon adsorber 5. This cumene recovery system could be utilized particularly with the lower pressure oxidizers 1.

The non-condensed off-gases may be conducted to a thermal oxidizer 6, connected to the condensers 3, 4 for treating the off-gases.

According to another preferred embodiment, the apparatus further comprises separate two-stage air (or other oxygen containing gas) scrubbers 8, 9 for purifying the air to be conducted into the lower pressure reactors 1 and the higher pressure reactors 2, as well as separate air compressors 10, 11 for compressing the air to be conducted to the scrubbers 8, 9.

The oxidation process and the apparatus of the present invention may be used for oxidizing any organic compound into its hydroperoxide. Preferably, the apparatus is arranged in a phenol production process. The phenol production process typically comprises process steps, wherein phenol and acetone are produced through the oxidation of cumene to cumene hydroperoxide (CHP) and, subsequently, wherein the CHP is concentrated and cleaved into phenol, acetone and other cleavage products, which products are washed and desalted, and finally wherein the acetone is separated from the phenol and both products are purified.

Before the mentioned cumene oxidation step, the oxygen containing gas feed required for the oxidation and at least the recycled portion of the cumene feed are purified from acidic impurities, such as acids and sulfuric components using at least a caustic solution. Subsequently, the cumene is subjected to oxidation, such as dry oxidation, preferably using air as the required supply of oxygen. The concentration of the CHP formed during the oxidation is increased in a series of concentration steps.

According to a preferred aspect of the invention, the concentrated CHP is further processed, e.g. by subjecting it to a cleavage process. According to this preferred aspect, the obtained cleavage product mixture is conducted further to the distillation section of the phenol production process. In the distillation section, the cleavage product mixture is distilled, first in order to separate a crude distillate, containing, for example, acetone, water, cumene, AMS, hydroxyacetone and mesityl oxide, from a crude base product, containing, for example, phenol, acetophenone, carbinol, mesityl oxide and heavy hydrocarbons, and further to separate impurities from the product phenol and the product acetone.

According to the present invention, the oxidation is carried out either as a wet oxidation, i.e. in a solution comprising a basic compound, preferably a carbonate, a bicarbonate or a hydroxide, more preferably as a sodium or potassium salt, or as a dry oxidation, i.e. without the presence of any basic compound and without the presence of any aqueous phase in the oxidation reactors 1, 2. Preferably, the oxidation is carried out as a dry oxidation.

Pure cumene is preferably conducted to the bottom section of at least the first lower pressure reactor 1. It is within the scope of the invention for pure cumene to be fed to some or all of the reactors in the series. In one embodiment, pure cumene is fed to all reactors in the series. In a preferred embodiment, pure cumene is fed only to the first lower pressure reactor.

An oxygen containing gas is preferably fed to at least the first lower pressure reactor 1. It is within the scope of the invention for the oxygen containing gas to be fed to some or all of the reactors in the series. In the most preferred embodiment, the oxygen containing gas is fed to all reactors in the series.

The oxygen containing gas, preferably air, can be distributed equally into the cumene by an air sparger. The gas is preferably washed in a two-stage air scrubber 8, 9 before being distributed, using first a diluted caustic solution and then water in order to remove all acidic traces, such as $SO_2$ and $CO_2$, and then all caustic traces. This washing process is most preferably carried out as described in European patent application no. 07150212.

The cumene left unoxidized after passing the last oxidation reactor 2 can be separated from the CHP and recycled to be used as cumene feed after being washed. This recycled cumene is preferably washed using first a caustic solution, preferably containing 0.2 to 2.0% of NaOH, more preferably about 0.5% of NaOH, in order to purify it from acids, phenol and methanol, and then water in order to purify it from caustic traces. Likewise the condensates formed from the off-gases are combined and washed using first a caustic solution, preferably containing 0.2 to 2.0% of NaOH, more preferably about 0.5% of NaOH, in order to purify them from contaminants comprising acids, phenol and methanol, and subsequently using water, in order to purify them from excess caustic, phenol and methanol. These washing processes are most preferably carried out as described in European patent application no. 07150215.

The high-pressure oxidizers 2 are preferably operated with reducing liquid levels, and are more preferably placed at reducing elevations, so that the first reactor 2 operating at a higher pressure is operated with the highest liquid level, and is preferably placed at the highest elevation, while the last one is operated with the lowest liquid level, and is preferably placed at the lowest elevation (compared to the sea level). Thus, the oxidation mixture may be conducted from the first lower pressure reactor to the next one, and from the lower pressure reactors 1 to the higher pressure reactors 2, using a pump, whereas the only liquid driving force required for passing the oxidation mixture from the first higher pressure reactor to the next one is gravity, whereby, at this point no pumps are required. This results in a minimized residence time of the oxidation mixture in the higher pressure reactors 2. Further, there is no heat input from pumps affecting the CHP decomposition.

Lower pressure reactors are preferably positioned at ground level.

According to a preferred embodiment of the present invention, the higher pressure oxidation reactors 2 are operated at a pressure that is at least 1 bar higher than in the lower pressure reactors 1. Preferably, the higher pressure oxidizers 2 operate at a pressure of 1.01-10.0 barg, more preferably about 2.0-8.0 barg, even more preferably 2.5-6.0 barg, and most preferably 3.0-4.5 barg, whereas the low-pressure reactors 1 operate at a lower pressure, up to 3.0 barg preferably 0.01-3.0 barg, more preferably 0.01-2.0 barg, such as 0.05 to 1.5 barg or 0.05 to 1.0 barg.

The liquid inventories of the lower pressure reactors 1 are preferably larger compared to the liquid inventories of any of the higher pressure reactors 2. More preferably the difference in inventories is 30-500%, most preferably 150-300%. In the lower pressure reactors 1, the CHP concentration is low and high individual reactor selectivity is possible. The CHP production rate is such that the production of CHP per reactor liquid volume decreases downstream in the series of reactors.

One of the benefits of the invention therefore is the ability to have larger liquid inventories in the lower pressure oxidizer and concurrent better selectivity for a larger amount of oxidation mixture. Also, the lower pressure oxidizer does not need to withstand high pressures so the design pressure of such a vessel is lower. This allows therefore the lower pressure oxidation reactor to take the form of a tank. Moreover, this may be positioned at ground level and at a safer distance from the higher pressure reactors, if required by the space limitations of the plant. Conventional cumene oxidation set ups employ smaller and more expensive pressure vessels.

Thus, viewed from a further aspect the invention provides an apparatus for oxidizing cumene to cumene hydroperoxide using an oxygen containing gas, comprising
 a series of 3-8 oxidation reactors (1, 2) and
 a sparger in the bottom section of each reactor (1, 2) for evenly distributing the gas conducted into the reactor (1, 2),
wherein the reactors include at least one lower pressure oxidizer (1) in the form of a tank and at least one higher pressure oxidizer (2) in the form of a column, said lower pressure oxidizer (1) being connected to a lower pressure gas compressor and said higher pressure oxidizers (2) being connected to a higher pressure gas compressor.

Preferably, the term tank is used herein to denote a container in which the vertical dimension is less than twice the cross sectional diameter of the vessel. Alternatively or additionally, in a tank, flow of material can be in all manner of directions.

Preferably, the term column is used in this context to denote a container in which the vertical dimension is at least twice as large as the cross sectional diameter. In particular, oxidizer columns allow flow primarily in the vertical direction.

It will be preferred if all lower pressure reactors are in the form of tanks and all higher pressure reactors are in the form of columns.

The temperature generally decreases when going downstream from the first lower pressure reactor. Thus, the first reactor is operated at the highest temperature and the last reactor, i.e. the last higher pressure reactor, is operated at the lowest temperature.

According to an embodiment of the present invention, the operating temperature is 115-90° C., preferably 110-95° C. Generally, the temperature difference between first and last reactors in the series is greater the larger the number of reactors employed.

According to the present invention, the concentration of CHP at the outlet of the last oxidizer is preferably 22-32%, more preferably 24-28%.

Moreover, the CHP production rate is preferably 10 to 30 kg/m$^3$ of reactor volume, more preferably 15 to 25 kg/m$^3$.

According to a preferred embodiment of the present invention, the cumene hydroperoxide formed in the oxidation is concentrated subsequent to the oxidation. The concentration may be carried out using a concentrator 12 that preferably functions in 2-3 stages of distillation, more preferably 3 stages. The main goal of the concentration is to remove unreacted cumene from the reaction mixture containing the CHP. The first distillation stage may be either a flash evaporation or a distillation with reflux, preferably a flash evaporation. The following stage(s) is (are) distillation stage(s) with reflux. The last distillation stage functions with the smallest burden, since the largest portion of cumene is removed in the first stage(s). The removed unreacted cumene is preferably condensed and washed, and finally recycled to the oxidation step.

By using the process of the invention, the selectivity calculated on a molar basis from the cumene oxidation products:

$$CHP/(CHP+AcPh+DMBA+2DCP)$$

(DCP=dicumyl peroxide.) can be increased to over 94.5%, e.g. at least 94.7 or at least 94.9%. Cumene consumption relative to the formation of phenol can also be reduced using the process described herein.

The present invention provides significant savings in capital investment if, for example, the capacity of an existing plant is increased and the process area lacks the space required for any new equipment to be placed close to the existing oxidation area. According to the present invention, the lower pressure oxidizers 1 may be located at a distance from the higher pressure oxidizers 2, and the CHP may be pumped safely at low concentration to the existing higher pressure oxidizers 2. The present invention also provides savings in capital investment caused by a need for low oxidation air pressure and a decrease of the compressor power consumption.

The invention claimed is:

1. A process for oxidizing cumene to cumene hydroperoxide (CHP) using an oxygen containing gas, which process comprises
 conducting a cumene feed and an oxygen containing gas feed to at least the first oxidation reactor in a series of 5-8 reactors, thereby forming an oxidation mixture, and
 conducting the formed oxidation mixture from said reactor to at least one subsequent reactor,
wherein
 the reactors comprise a lower pressure oxidizer (1) as the first reactor in the series and higher pressure oxidizers (2) as the other reactors in the series;
 said lower pressure oxidizer is operated at a pressure of at least atmospheric pressure and said higher pressure oxidizers are operated at a pressure of at least 0.5 bar higher than said lower pressure oxidizer.

2. The process as claimed in claim 1 wherein there are 4 or 5 high pressure oxidizers.

3. The process as claimed in claim 1 wherein fresh oxygen containing gas is fed to all reactors in the series.

4. The process as claimed in claim 1 wherein cumene is fed only to the first reactor in the series.

5. The process as claimed in claim 1 wherein the higher pressure oxidizer is operated at a pressure of at least 0.5 bar higher than the lower pressure oxidizer.

6. The process as claimed in claim 1 characterized by washing the oxygen containing gas with diluted caustic and water to remove all acidic or caustic traces before conducting it into an oxidation reactor.

7. The process as claimed in claim 1, characterized by operating the oxidation as a dry oxidation.

8. The process as claimed in claim 1, characterized by operating the higher pressure oxidizers (2) with reducing liquid levels so that the liquid level of the first high-pressure oxidizer (2) in the series is highest.

9. The process as claimed in claim 1, characterized by maintaining larger liquid inventories in the lower pressure oxidizer (1) than in any of the higher pressure oxidizers (2).

10. The process as claimed in claim 1, characterized by operating the oxidation at a pressure of 0.01-3.0 barg in the lower pressure oxidizer (1), and 1.01-10.0 barg, in the higher pressure oxidizers (2).

11. The process as claimed in claim 1, characterized by producing an oxidation product having a CHP concentration of 22-32%.

12. The process as claimed in claim 1, wherein oxidation mixture is transferred to each reactor in series.

13. The process as claimed in claim 1, characterized by removing unreacted cumene in the top gas from at least one reactor in the series, condensing the cumene, combining the unreacted cumene in the formed condensates and subsequently washing the condensed cumene using a caustic solution, in order to purify them from contaminants comprising acids, phenol and methanol.

* * * * *